United States Patent [19]

Thomé et al.

[11] Patent Number: 4,463,609
[45] Date of Patent: Aug. 7, 1984

[54] METHOD AND APPARATUS FOR TESTING THE SOUNDNESS OF THE WELDS OF OFF-SHORE STRUCTURES DURING SERVICE

[76] Inventors: Paul Thomé; Gopal Thomé, both of 8 rue Coutureau, Saint Cloud, France, 92210

[21] Appl. No.: 335,321

[22] Filed: Dec. 28, 1981

[30] Foreign Application Priority Data

Dec. 29, 1980 [FR] France .................. 80 27714

[51] Int. Cl.³ .......................................... G01N 29/04
[52] U.S. Cl. ................................................. 73/637
[58] Field of Search ............ 73/637, 640, 633, 40.5 R, 73/622; 324/226, 261, 262

[56] References Cited

U.S. PATENT DOCUMENTS 3,327,206  6/1967  Wood et al. .................. 324/261
4,389,894  6/1983  Kajiyama ...................... 73/637

FOREIGN PATENT DOCUMENTS 2537613  3/1977  Fed. Rep. of Germany ........ 73/633
55-42022  3/1980  Japan ............................. 73/637
2012047  7/1979  United Kingdom ................ 73/637
456204   3/1975  U.S.S.R. ........................... 73/637

*Primary Examiner*—S. Clement Swisher
*Assistant Examiner*—Brian R. Tumm
*Attorney, Agent, or Firm*—Holman & Stern

[57] ABSTRACT

Ultrasonic probes are automatically moved and oriented on the edges of a weld in off-shore structures. An open U squirrel cage is fixed on a secondary member of an off-shore structure; an open U squirrel cage rotor rotates in the squirrel cage and bears a retractable sleeve within which an inspection arm moves. The end $\Omega$ of the arm has an orientable telescopic elbow of length $\Omega\Gamma$. From a wrist $\Gamma$ of the arm extend two hands bearing ultrasonic feelers. The position of $\Gamma$, the angle of the hands between them, and their orientation, are programmed by numerical control from theoretical geometries. The compensation of the manufacturing tolerances is integrated into the design of the hands. The device is useful for checking the welds of nodes in off-shore platforms.

5 Claims, 17 Drawing Figures

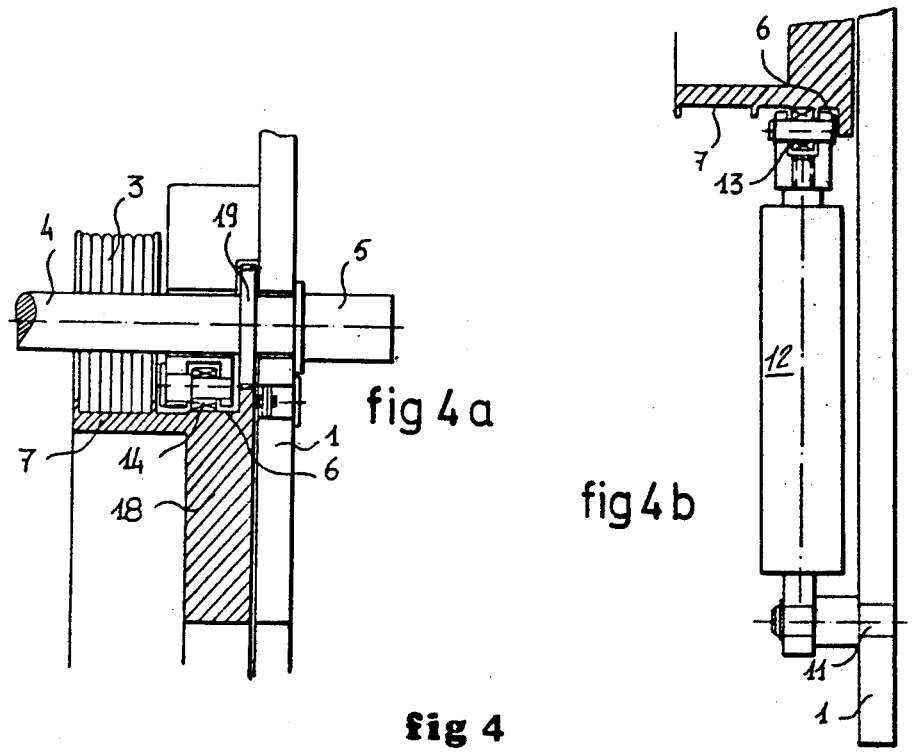
fig 4
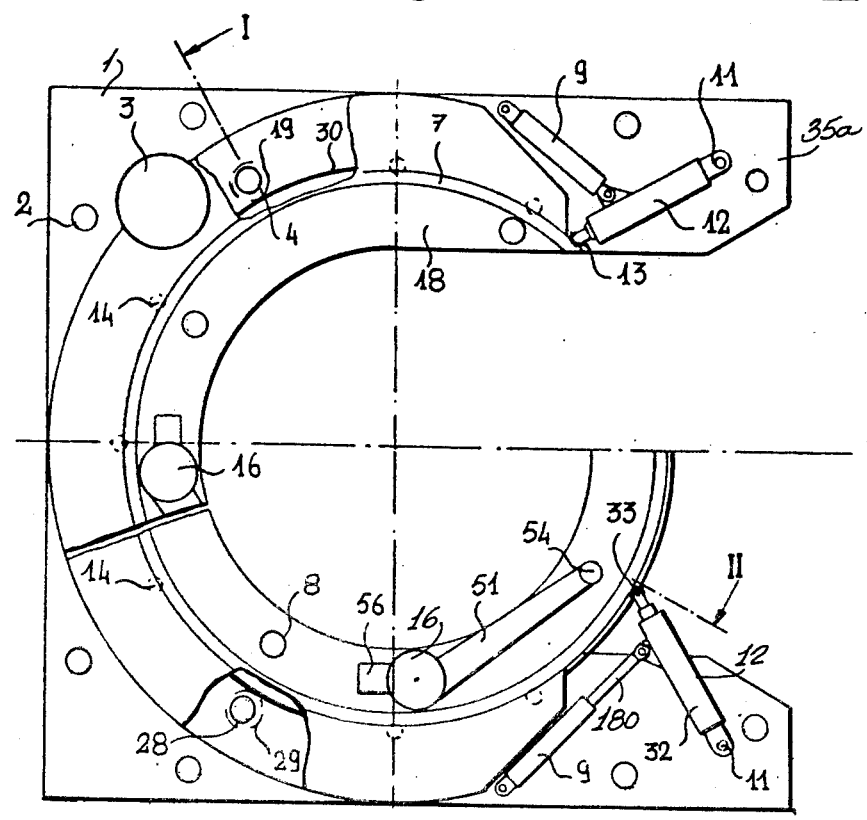

METHOD AND APPARATUS FOR TESTING THE SOUNDNESS OF THE WELDS OF OFF-SHORE STRUCTURES DURING SERVICE

FIELD OF THE INVENTION

The present invention relates to the checking of offshore structures during service of the type used for prospecting and exploiting petroleum deposits. More especially the invention relates to certain mechanical devices suited for the often gigantic tubular trellis assemblies which constitute the immersed mechanowelded structure. The invention also relates to particularly sensitive and effective testing methods for the systematic and automatic examination of the entire welds of such structures, in a hostile environment.

The increasing needs of energy, aggravated by political problems, encourage the exploitation of sub-marine petroleum deposits, resulting in the appearance of a multitude of drilling and exploitation off-shore platforms which can be of colossal size. These "works" are intended to last some 15 years or more and represent considerable investments. Their progressive or accidental deterioration at sea involves risks to human life and may be irremediable for the equipment. It is hence indispensable to monitor the condition of these structures constantly.

For the most part, these structures are mechanowelded, constituted from a criss-crossed tubular trellis comprising, principal members (shafts or piles) and secondary members (bracings). The diameters of these members vary from some tens of centimeters to several meters. The nodes, where several bracings converge on the same shaft, comprise up to six to eight bracings, with or without stiffening gussets. The welds amount to hundreds and they coincide with particularly stressed zones, capable through their nature and their location of being the sites of cracks and faults in fabrication.

DESCRIPTION OF THE PRIOR ART

The detection of the cracks which will appear and develop in the course of time, through fatigue, through corrosion, etc., is at present done by divers. This amounts to a non-exhaustive visual check, assisted by measuring tools carried by the divers (e.g., magnetoscopy and ultrasonics). In addition, attempts are becoming current to use manned or unmanned submersible vehicles instead of divers. The arms or manipulators equipping these vehicles reproduce the operations of the diver. These methods are far from being efficient and they are not satisfactory for application of accurate and reproducible testing methods which demand firm and accurate positioning to within some millimeters of the measuring probes. Again divers, like vehicles, become lost in the multitude of members, nodes and welds. Confusion is frequent in identifying and following the development of an anomaly.

From its installation, a platform is provided with a series of measuring gauges intended either to monitor and check the positioning operations, or to measure the stresses to which the platform is subjected and to reset these measurements with mathematical models. However, this instrumentation has a limited lifespan, and this is the same for any checking probes intended to detect cracks. Through their quantity and their location, the maintenance of these instrumentations fixed on the members becomes rapidly impossible. Current methods hence do not permit the inspection during operation needed by reproducibility of the measurements as well as the transcription of the experimental date: e.g., the precise identification of the position of the fault, its dimensions, and its orientation.

To reduce the technological difficulties associated with non-destructive testing by point probes (coming into the immediate proximity of a fault), it is necessary at present to use indirect testing methods, such as diagnosis by acoustic emission (based on listening for the noise emitted by the development of a crack), or such as a spectrum analysis of the vibrations of the structure at precise points (forced excitation or natural vibrations). In fact, it is speedier and simpler to place a probe and an energizer on a member than to make an examination by a precise mechanical scanning of the weld by a probe. Obviously, the sensitivities of the methods are not to be compared.

Acoustic emission, like the spectrum analysis of the vibrations, are testing methods, which are not exhaustive and which are applied to simple geometries and to point operations.

It is an object of the invention to provide a device for checking the soundness of welds in off-shore structures during service by a method which is direct, exhaustive, accurate, reproducible, rapid and this without having to resort to divers.

It is a further object of the invention to provide a testing device particularly adapted for the examination of the welds of nodes in such structures. It is a further object of the invention to provide a testing device permitting the firm positioning and orientation of measuring probes accurately to within some millimeters with respect to the weld bead (scanning of the weld).

It is a further object of the invention to provide a device enabling the rapid installation and rigid fastening of such a testing system on the members of an off-shore structure.

Other objects and advantages of the invention will become apparent from the description which follows.

SUMMARY OF THE INVENTION

According to the invention, there is provided a device for testing the integrity of off-shore structures whilst in service, said device comprising one or several probes (ultrasonic, eddy current or the like) which are mechanically (and not manually) placed in the immediate proximity of the weld, and whose orientation is a function of the position of the point being explored.

In a particular embodiment of the device, checking is effected by ultrasonic waves, the one or more probes being in contact with the member being examined (hereafter "the member") and arranged so that the transverse waves emitted are parallel or perpendicular to the plane of cross-section of the weld at the point concerned so as to detect either cracks transverse to the weld or cracks along the weld. The placing of the probes relative to the weld is defined to within some millimeters and is known at any moment, which is indispensable for the retranscription and analysis of the signals. The position of the probes on the member is known to within some centimeters.

In a preferred embodiment of the invention there is provided an automatic device, scanning system, or orbital scanner (hereinafter "scanner"), comprising an open U-shaped fixed structure, which by transverse movement can come into astride position on the member, and which is equipped with fixed jacks or clamping jaws; and a movable structure formed from shaped rotary plates centered on an open bearing borne by the fixed part, which permits regular orbital movement of the movable structure within the fixed structure in spite of the U-shaped opening.

The fixed structure is centered on the member by a set of jacks which, after centering, define the theoretical axis of the member. The movable structure rotates around this theoretical axis which is also that of the scanner. This structure bears a retractable sleeve carrying a column or arm which slides parallel to the member. At the end of this arm is a wrist to which is affixed an inspection mechanism having one or several measuring heads and associated examining probes. The measuring heads are endowed with several degrees of freedom in the mechanical sense of the term, by means of which the geometric tolerances of ovalization of the one or more members and the manufacturing tolerance (squeezing of the members against one another) are taken into account.

The purpose of the measuring head is to maintain the Examining probes in the immediate vicinity of the weld bead, in a precise orientation with respect to the latter, and in contact with, if not in the immediate vicinity of the corresponding member.

The detection of the cracks, their marking, their orientation and their size determination are done by Examining probes bearing a series of ultrasonic transducers (perpendicular sensors and angular sensors) according to methods well known in automatic control systems carried out on circuits of nuclear power stations.

BRIEF DESCRIPTION OF THE DRAWING

In order that the invention may be more fully understood, a particular embodiment is described below purely by way of illustrative example, with reference to the accompanying drawings in which:

FIG. 4 corresponds to the view along the line IV—IV of FIG. 2.

FIG. 4a and 4b are respectively cross-sectional views according to I and II of FIG. 4;

DETAILED DESCRIPTION OF THE INVENTION

Figure 1A:
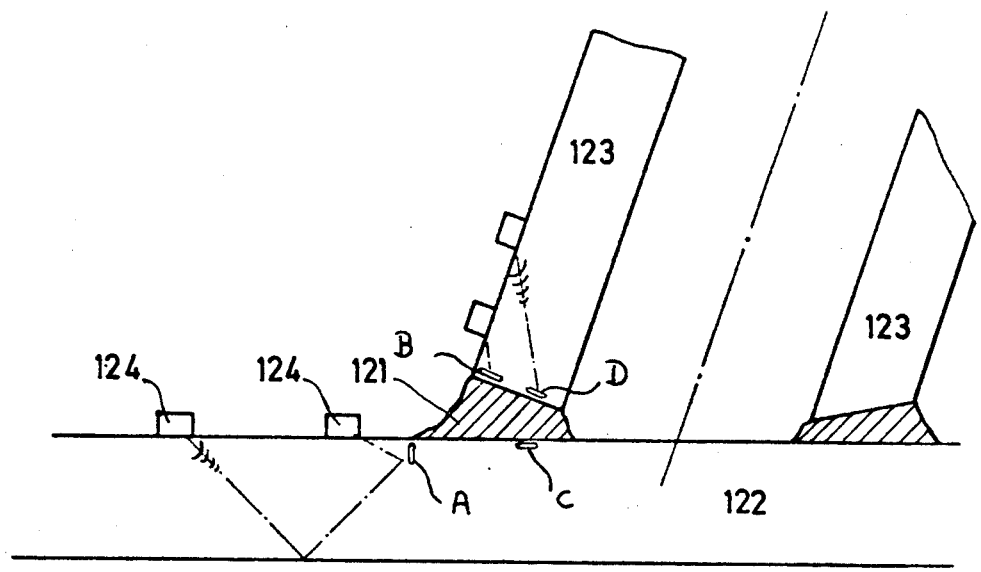
FIGS. 1a and 1b show diagrammatically welds between members in which the presence of cracks is being detected.
Figure 1B:
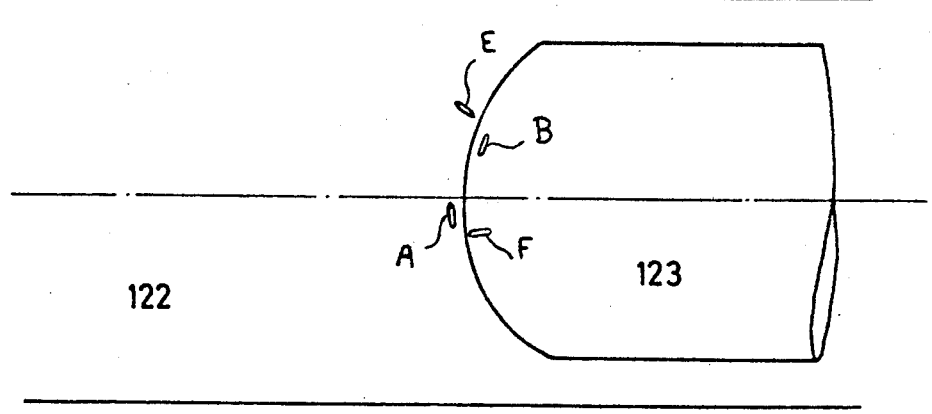

The cracks which are to be detected are illustrated in FIGS. 1a and 1b. Conventional fatigue cracks (A and B in the Figures.) which are perpendicular to the surface of the member and parallel to the bead, are easily detected and measured; similarly, those cracks which result from a fault in lamination or from adhesion (C) on the principal member, or rom adhesion to the secondary member (D) will be detected by angular feelers on the secondary member; as will all those which depart from the bead in any direction whatever (E, F).

The scanner is shown in FIGS. 2, 3, 4, and 5. The scanner includes a fixed structure 80 comprising three plates or flanges in U form: a front flange 20, an intermediate flange 1 and a rear flange 34; they are connected to one another by tie rods 2 which confer on the fixed structures 80 its rigidity. On the rear surface of the intermediate flange 1 and on the front surface of the rear flange 34 are fixed jacks 49 having gripping jaws 51 which are withdrawn on the positioning or the withdrawal of the scanner and which are activated to grip a member 123 during testing.

Figure 2:
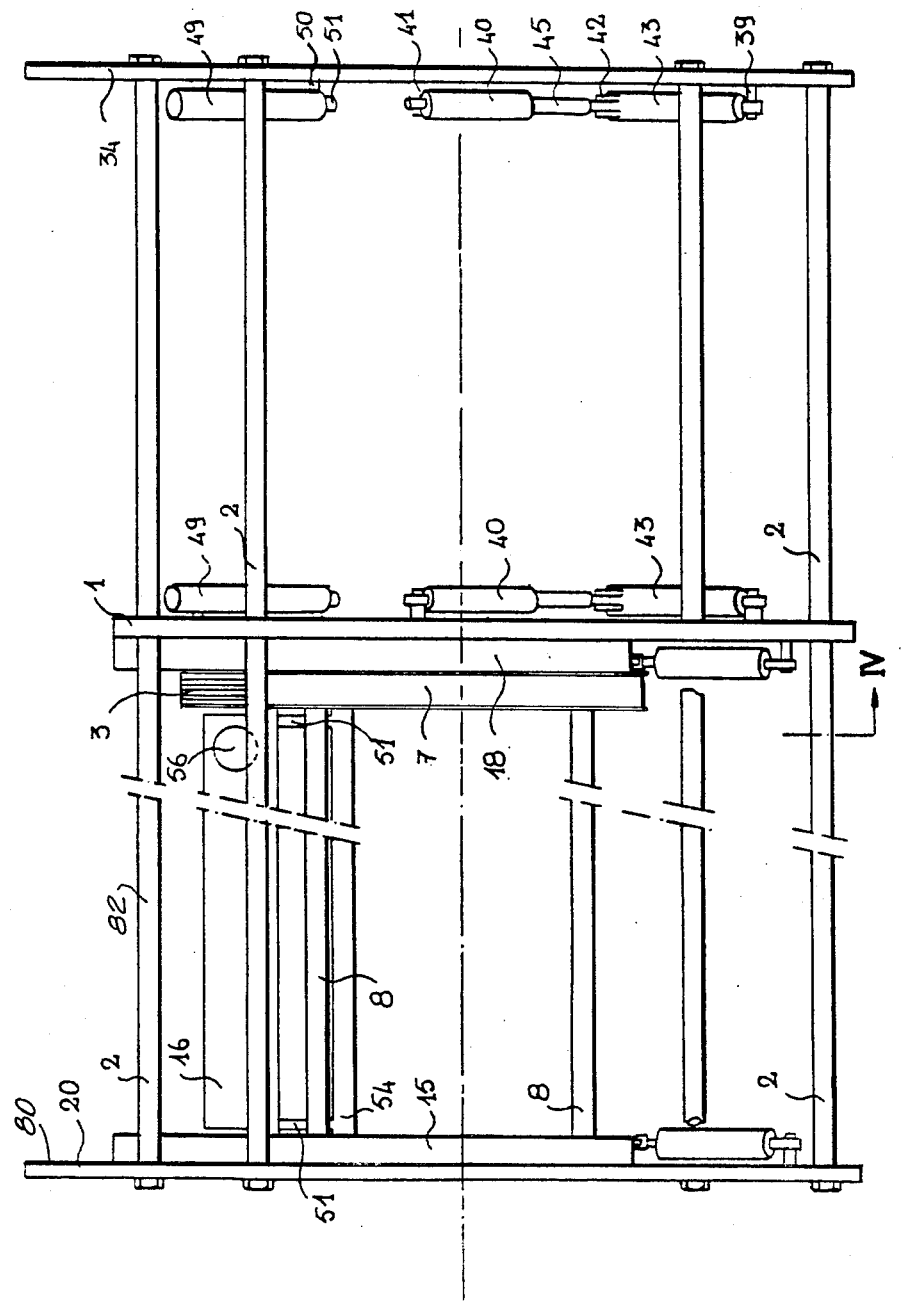
FIG. 2 is a plane view of a scanner device according to the invention which has come into position to check a member horizontally.
Figure 3:
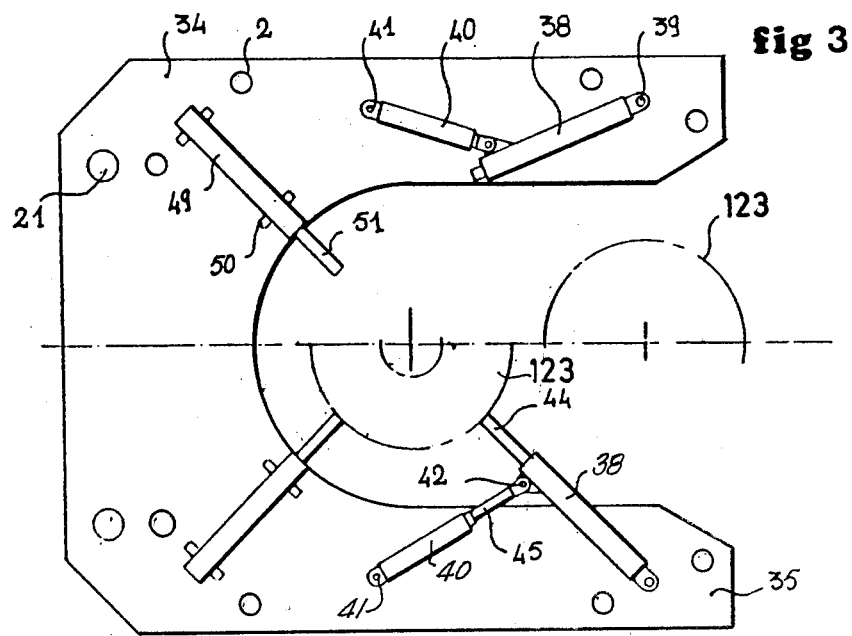
FIG. 3 shows the front surface of the rear flange of the embodiment according to FIG. 2.

FIG. 2 is a plane view of the scanner which has come to grip a member horizontally. FIG. 3 shows the front surface of the rear flange 34. It should be noted that the rear surface of the intermediate flange 1 is quite similar; it contributes to ensuring a firm grip on the member. In FIG. 3 it is seen how the scanner is placed on the member 123 and how it will be clamped thereon.

A plurality of pivotable jacks 38 situated on legs 35 of the U-shaped flanges 1 and 34 are in withdrawn position when the scanner is going to be engaged on the member 123. These pivotable jacks 38 pivot around an axle 39; this evading movement is actuated by actuating jacks 40 connected by hinges 42 to the pivotable jacks 38; the actuating jacks 40 pivot around a point 41. When the scanner is completely engaged on the member 123, the pivotable jacks 38 pivot between the positions shown in FIG. 3 due to the emergence of a rod 45 from the actuating jack 40; the pivotable jack 38 then closes on the member 123 with jaws 44. At the bottom of the U-shaped flange 34, fixed jacks 49 fixed by yokes 50 complete the gripping through their jaws 51. The apertures 21 situated at the base of the U, in the front and the rear flanges 20 and 34 are designed to permit hooking and holding of the scanner by a lifting system.

Figure 5:
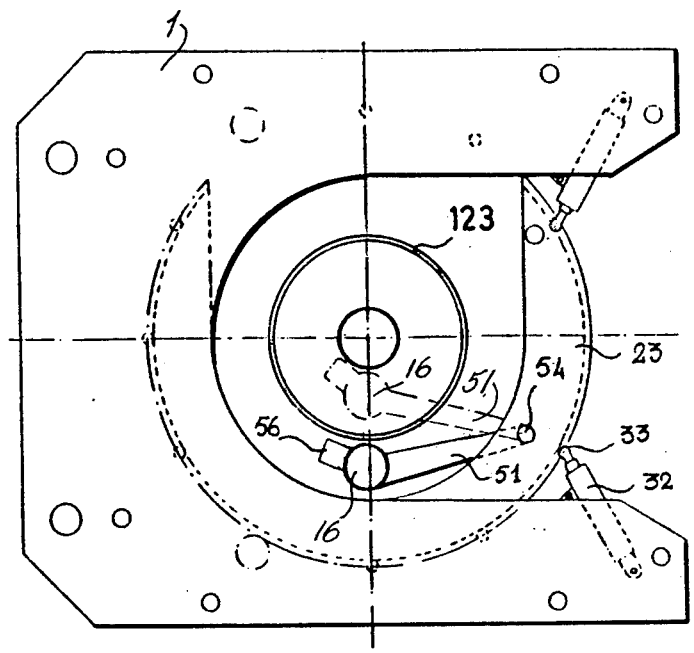
FIG. 5 is a side view of the scanner of FIG. 2 showing the position of the moveable structure after rotation through 90°.

The rear surface of the front flange 20 and the front surface of the intermediate flange 1 possess bearings on which the movable structure 82 rotates. This is illustrated in FIGS 2, 4 and 5.

The intermediate flange 1, traversed by tie rods 2, bears at the ends of its legs 35a eclipsable elements 12 (FIG. 4) bearing at their ends rollers 13; eclipsable jacks 9 associated with elements 12 cause the elements 12 to pivot around their axes 11 by extension of a rod 180 associated with jack 9. After the positioning of the scanner, these elements 12 are pivoted to the position shown at 32 and the rollers 13 come to complete the guide path at 33 defined by flange roller 14 of glanges 20 and 1.

The moveable structure of the scanner is a U-shaped "squirrel cage" 82. It comprises two U-shaped circular plates, 15 and 18 (FIG.2), which rotate respectively on the rollers 14 of the flanges 20 and 1 (FIG. 4), and which are connected by tie rods 8. The plates 15 and 18 roll through their cylindrical surface 6 (FIGS. 4a and 4b) on the rollers 14.

The plates 15 and 18 are rotated simultaneously by a motor 5 (FIG. 4a) fixed at 1 actuating a first driveshaft 4 which engages a rack 30 (FIG. 4) through a gear 19. A second driveshaft 28 coupled to the first driveshaft 4 ensures the continuity of rotation of the movable structure 82, despite the U-shaped opening, through a drive gear 29, which also engages the rack 30. The moveable squirrel cage structure 82 bears a retractable sleeve 16, parallel to the tie rods 8. This sleeve 16 is held by rods 51 fixed to an axle 54. The retraction is actuated by a motor (not shown), fixed at 18. In this sleeve 16 is placed a control arm 101 which will be described below.

Figure 7:
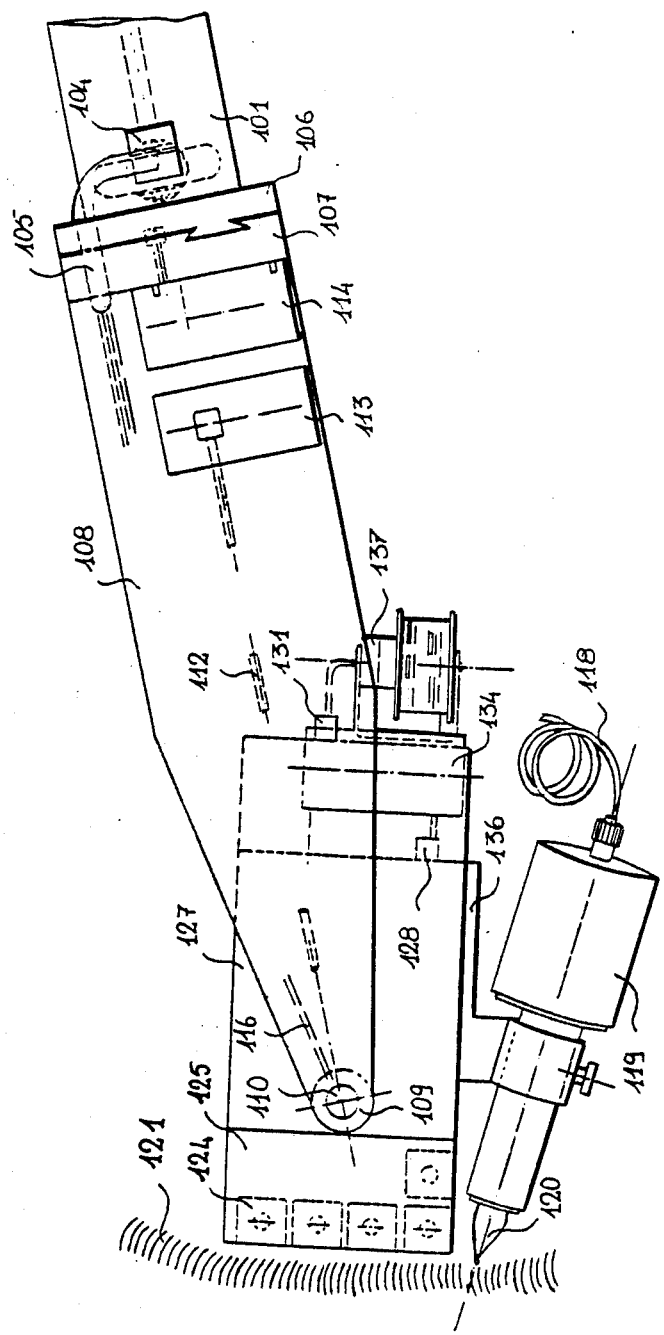
FIG. 7 is a plane view of the arm of FIG. 6.

The drum 7, supporting cables, is fastened to plate 18. Cables, and the like, for electrical supply, for hydraulic supply and the like, which come from the fixed structure 80 to the movable structure 82, are borne by a spool 3 which rotates at the same time as drum 7 so as to keep the cable taut. A cylindrical connector 110 (FIG. 7) ensures the connection of the fluid supply and electrical supply cables as well as the connection of the instrumentation cables, etc., between the fixed and movable structures 80 and 82.

In FIG. 5 is indicated the position at 23 of the plates after rotation through 90°, when the checking of the member 123 is under way. The U-shaped plate is engaged on the rollers 33 of the eclipsable elements 12 in position 32. The sleeve 16 is in retracted position.

Figure 6:
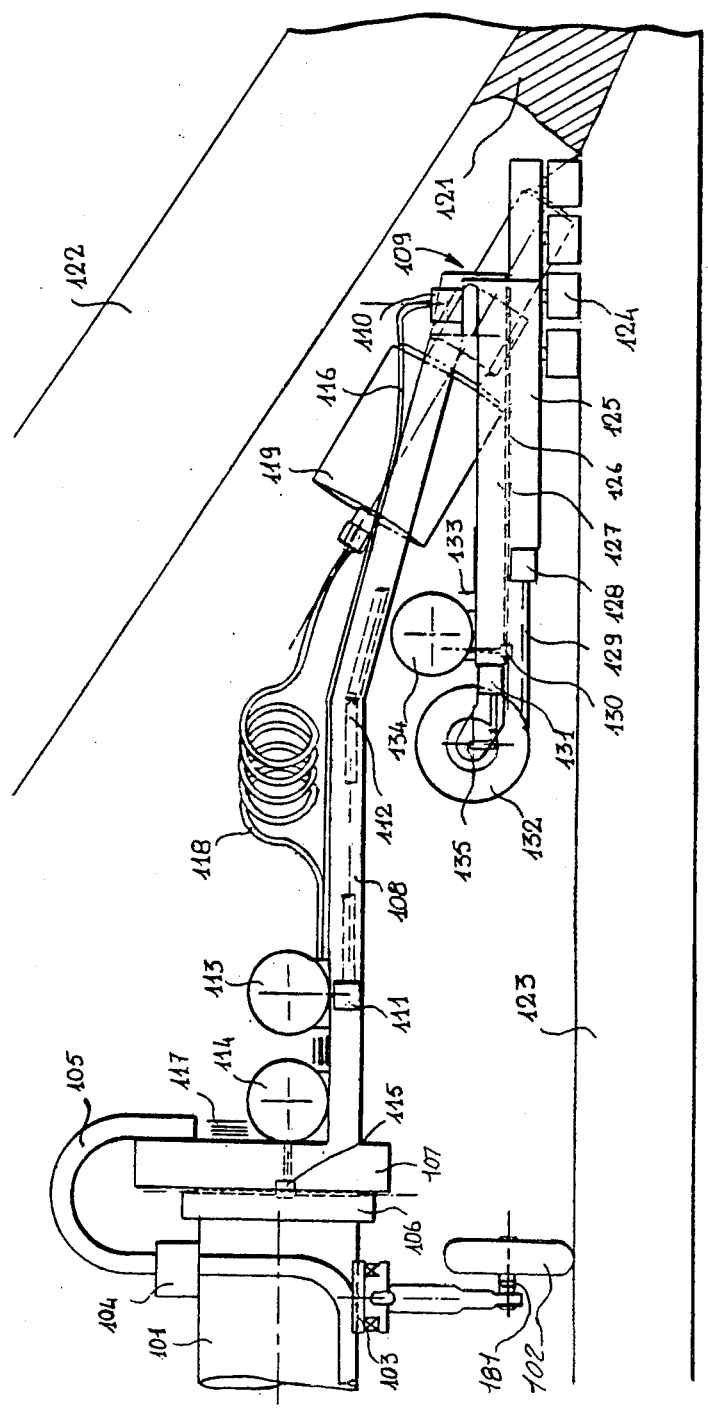
FIG. 6 shows in elevation, the end of the arm and the intersection of the members being checked.

Inside the sleeve 16 is the control arm 101 (FIG. 6). The orientation of this arm is actuated by a motor 56 so that the arm 101 is always directly facing the member 123 despite the rotation of the sleeve 16 on the axle 54. During inspection, this arm 101 is extended out of the sleeve 16 servo-coupled to the angular position of the movable structure 82. A stepping motor and a transmission located inside the sleeve 16 (not shown) ensure this movement.

We will describe two features designed to move ultrasonic examining probes in the immediate vicinity of the bead on the member 123. According to the first, explained in FIGS. 6 and 7, ultrasonic probes are moved exclusively over the surface of the member 123 on which the scanner is placed.

The end of the arm 101 is held by a wheel 102, at 103 and mounted on a spring or damper 181. The various instrumentation and electrical supply, and even fluid supply, cables arrive at a coupling plug 104 on arm 101. This arm 101 is parallel to the secondary member 123 (secondary because it is totally intercepted by a primary member 122) whose weld 121 is to be checked.

At the distal end of the arm 101 is fixed a slide table which forms the connection with the wrist 108. This slide table has a plate 106 fixed to the arm 101 and another plate 107 fixed to the wrist 108. The movements of the arm 101 are directed towards the axis of the scanner (radially) and they are actuated and programmed by a first stepping motor 114 and its transmission 115. The supply cables 105 are fixed at 117 to the plate 107.

The "hand" is attached to the end 109 of the wrist 108. It rotates around an axis directed radially. This rotation is actuated and programmed by a second stepping motor 113 with its transmissions 111 and 112 engaging a crown wheel borne by a rotary axle (not shown). Supply and instrument cables 116 borne by the wrist 108 arrive at a cylindrical collector 110 borne by the axle.

The hand includes a slide table parallel to the member 123 (parallel to the axis of the scanner). It is oriented constantly perpendicular to the weld bead 121 by rotation of an upper plate 127 actuated by the motor 113. It carries a motor 134 having a electrical connecting plug 133, which, through a transmission gear 130, engages an endless screw 126, which provides for the movement of a sliding lower plate 125. Under this sliding plate 125 and its distal end are located ultrasonic probes or transducers 124. The instrument cables of these transducers 124 are taken up by a terminal 128 and a cable connector 129. The cable 29 is kept constantly taut by the winding drum 132 fixed by a yoke 135 to the upper plate 127. A rotary electrical collector 137 (FIG. 7) is connected to the upper plate 127 by a plug 131. A joint follower 119—conventional equipment in welding technology—supports its follower finger 120 moves away from its axial position shown in FIG. 7. Data are immediately retransmitted through cables 118 to the level of the motors 114 and 134 which respectively control the radial position of the hand (that is to say which control the support of the probes 124 on the member) and the progress of the probes up to the immediate vicinity of the weld bead 121 by extension of retraction of the hand. This feed-back, which repositions the finger 120 in equilibrium position in the axis of the joint follower 119, ensures the following of the bead 21 by the probes. Also, servo-coupled to the angular position of the arm 101, are, first, the wrist 108 (by programming of the extension of the telescopic arm), and second, the orientation of the hand with respect to the arm (by programming of the motor 113). This servo-coupling results from a theoretical calculation done by numerical control of the scanner from the theoretical intersection of the two cylinders representing the members. In fact, to each point of this intersection there corresponds a single point on the secondary member 123 situated at a constant distance (length of the "hand") which is predetermined in the plane perpendicular to the tangent to the intersection. In other words, in the case of a perfect mechanical assembly, the programming of the extension of the arm 101 and of the orientation of the hand will suffice to ensure mechanically correct positioning of the probes 124. The movements along two slide tables are essentially intended to absorb the manufacturing tolerances, and the knowledge of these tolerances is provided by the joint follower 119, which actuates the necessary corrections.

The second feature explained below is developed in the simultaneous control of two sides of the bead 121 from the surface of each of the members 122 and 123 (principal and secondary). It is explained in FIGS. 8, 9, 10 and 11.

Figure 8:
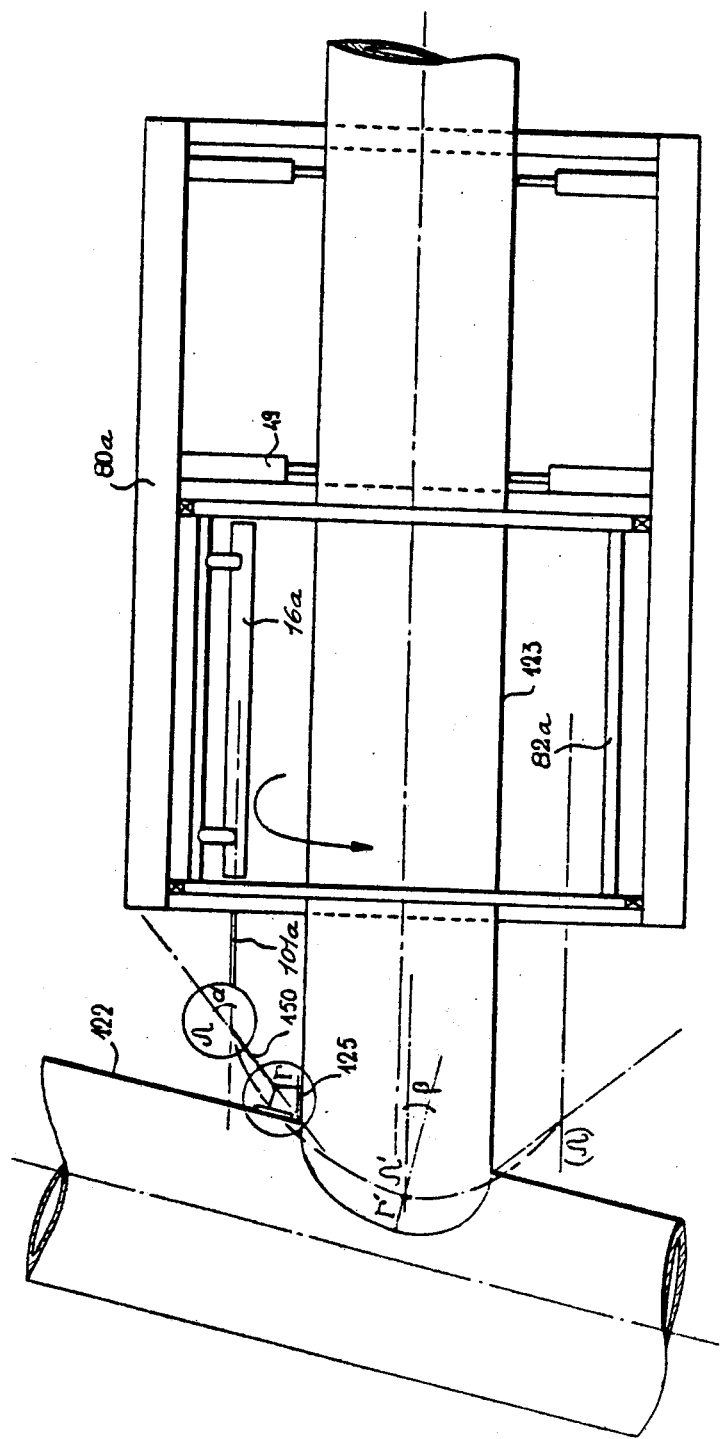
FIGS. 8, 9, 10 and 11 illustrate the operation of the feeler hands extending from a wrist on a telescopic lever.
Figure 9:
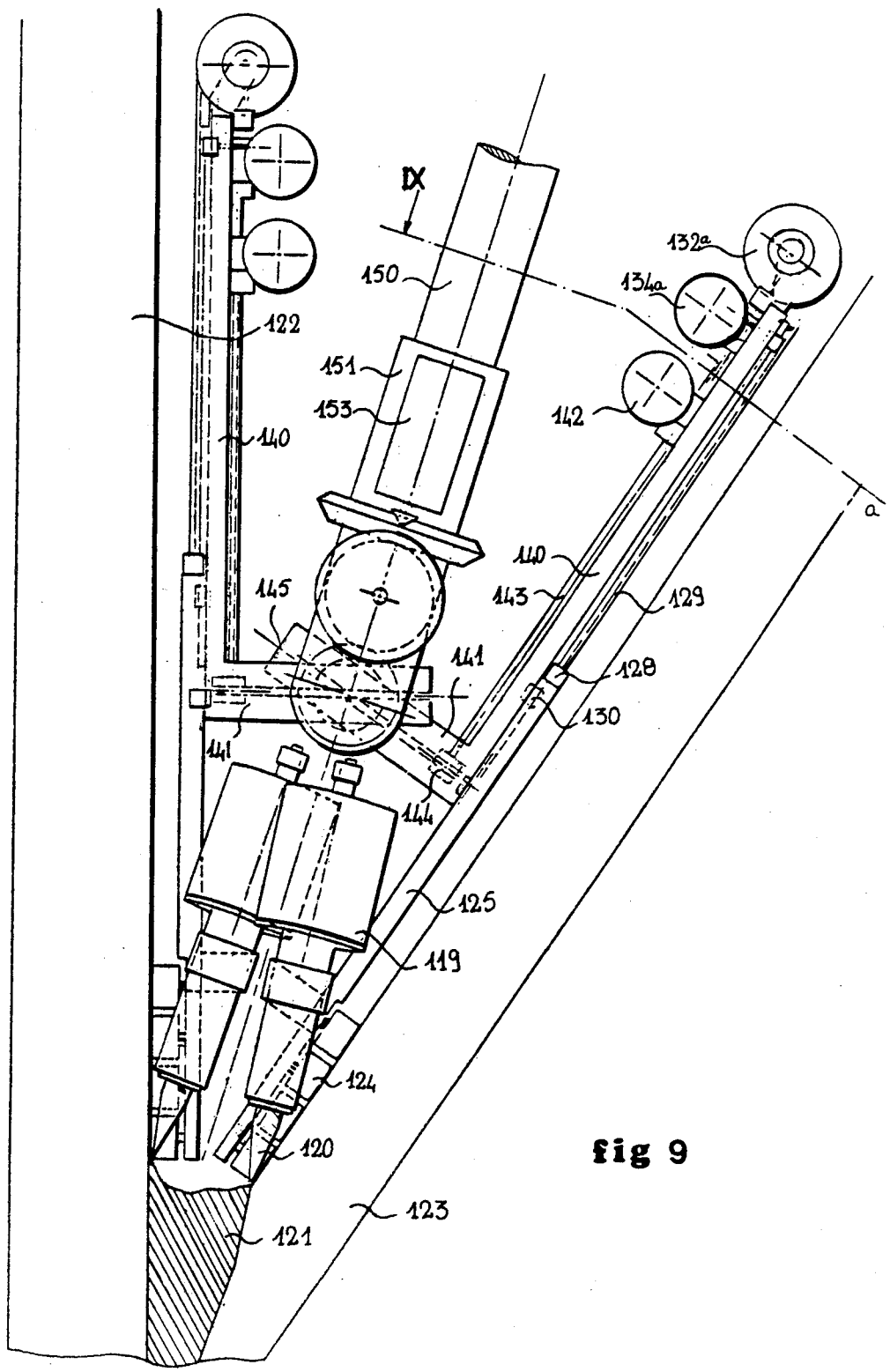

In FIG. 8 is shown diagrammatically the purging of the scanner. The fixed structure 80a of the scanner is fastened by the fixed jacks 49 of the secondary member 123. The U-shaped movable structure 82a possesses a retractable sleeve 16a from which an arm 101a emerges. The end Ω of the arm 101a includes an articulation for a lever 150 of adjustable length. On this lever 150 the point Γ describes in space a curve programmed in advance from the theoretical geometries of the node. The lever 150 is oriented in the plane perpendicular to the tangent of the weld bead at the point subjected to checking; this is the bisector of the tangents of the members 122 and 123. From the point Γ leave two exploration heads (not shown) applied on each of the members 122 and 123. The point Ω describes a curve (Ω), calculated, on a secondary member 123; it is at Ω when the secant plane is at the front (FIG. 8). The length ΩΓ of the lever 150 is also programmed so that the exploration heads are fastened against the theoretical position of the members 122 and 123; it is the same for the corner formed between the two exploration heads.

Figure 11A:
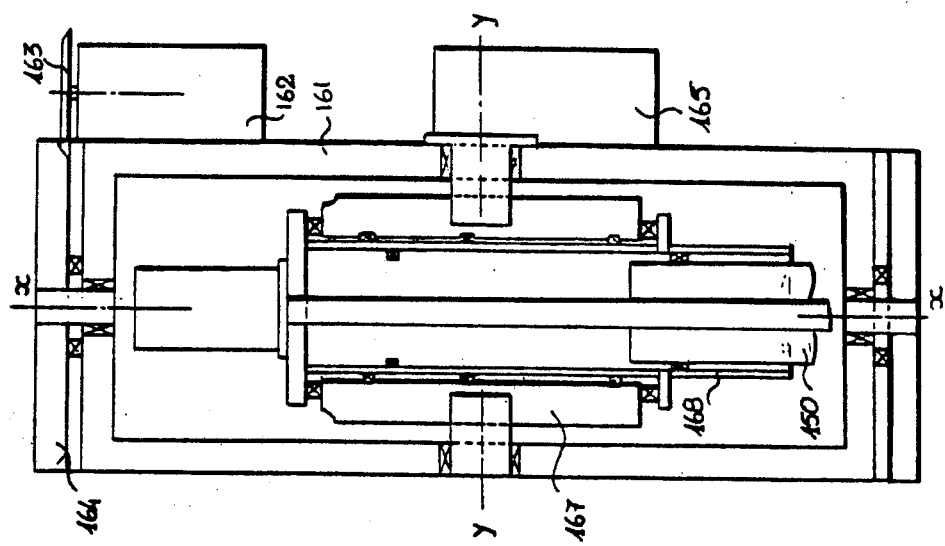
FIG. 11a is a cross-sectional view according to the line x—x of FIG. 11.
Figure 11:
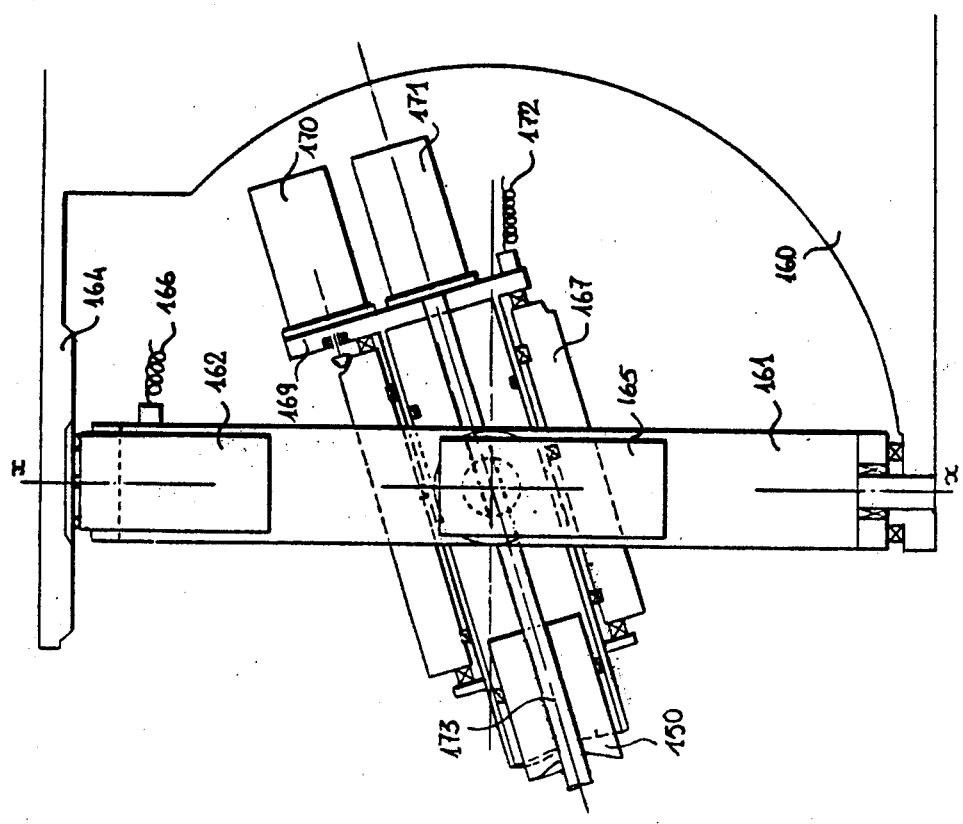

An end 160 of the arm 101a (FIG. 11) includes an elbow (cardan) defined by the two perpendicular axes of rotation Xx, Yy. The axis Xx is perpendicular to the secondary member 123. On this elbow is fixed the telescopic lever 150. The control unit is shown in FIG. 11. Armature 161 of the elbow pivots on the axis Xx; this movement is actuated by a motor 162 whose drive pinion 163 rolls on a circular toothing 164 of end 160 of arm 101a. The inclination of the lever 150 is controlled by a motor 165 affixed to armature 161. The electrical supplies are shown symbolically by 166.

For a given inclination, the position of the lever 150 is defined by two parameters: its extension and its orientation with respect to its axis. This is done in the following manner. The inclination is defined by a jacket 167 which pivots around Yy. Within this jacket is fixed a collar 168 with a flange 169 bearing motors at 170 and 171 for the orientation and extension of the lever 150. The electrical supplies as well as the instrument cables are shwon symbolically at 172 as connected to flange 169. The motor reducing gear 171 has a drive pinion which engages a rack located at 167. The motor reducing gear 171 actuates an endless screw 173 which drives the outlet of the lever 150.

Figure 10A:
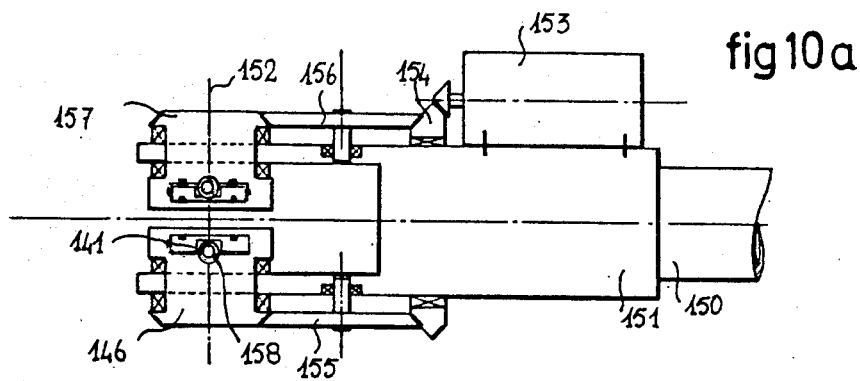
FIG. 10a is a cross-sectional view according to B of FIG. 10.
Figure 10:
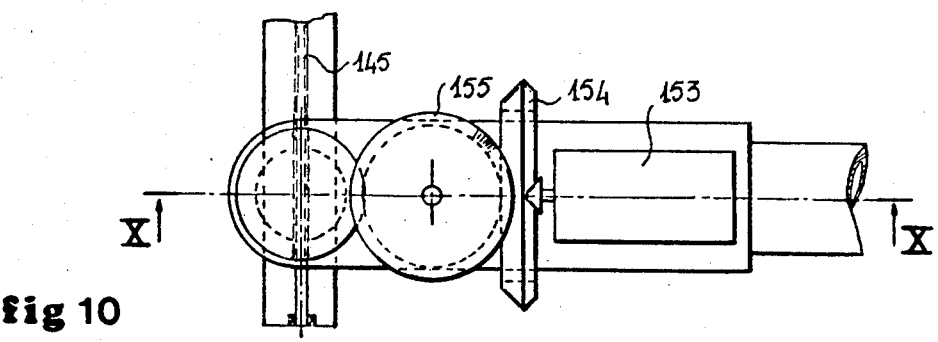
Figure 9A:
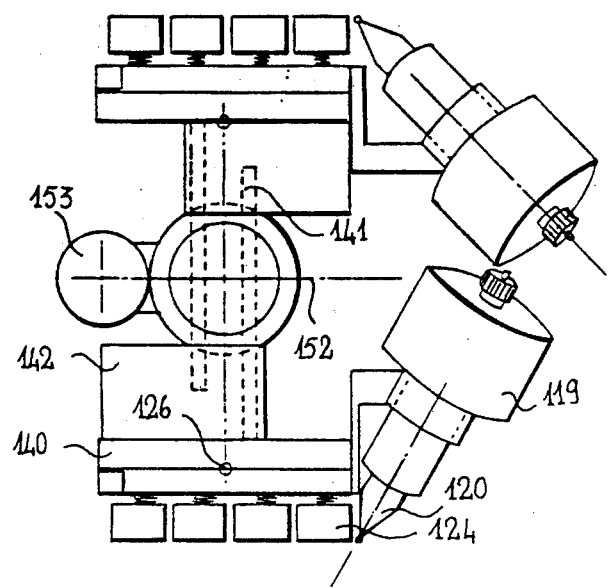
FIG. 9a is a cross-sectional view along the line 4 of FIG. 9.

From the elbow, the telescopic lever 150 departs going up to the wrist 151. At the end of the wrist 151 is fixed an axle 152 (FIGS. 8, 9, 10) around which two feeler hands 146 and 157 pivot through an angle, in contrary directions on each member. The pivoting of the hands is actuated by a motor 153 driving a crown wheel 154 coaxial with wrist 151 and which, through the shaft of the gears 155 and 156, causes feeler hands 146 and 157 to rotate in opposite directions (FIG. 10). The hands include a flat upper plate 140 (FIG. 9a), which is positioned parallel to the controlled member; this plate 140 is extended by a perpendicular arm 141 which slides inside the feeler hand 146. This translation is actuated by a motor 142, through an axle 143 and a transmission 144, which rotate an endless screw 145 fastened to arm 141. Inside feeler hand 146 is imprisoned a nut 158 traversed by the screw 145. On upper plate 140 are situated a motor 134a and a drum 132a having a role identical with that which was described in the preceeding example. The hand also includes a lower sliding plate 125, with feelers 124 at its end intended for the ultrasonic checking, and follower 119 with its contact finger 120. The translation of lower sliding plate 125 is actuated by the motor 134 and by the cable connector 129 and the transmission gear 130; a drum 132 keeps tight the cable connector 129 connected to lower sliding plate 125 by plug 128.

Prior to testing, it is necessary to free the surfaces of all their concretions, such as algae and calamine. To do this, a device similar to those which have just been described is used, by adapting to the wrist a conventional portable tool such as a rotary metallic brush or, high pressure water jets.

All of these devices enable the automatic checking of welds of the nodes of off-shore platforms. Systems for positioning the scanner on the members depend essentially on the design of the platforms and their complexity; they are not the subject of the present patent.

We claim:

1. A scanner device for testing at a distance the presence of cracks in a assembly of welded tubular members, such as member nodes or tappings, said device having examining probes adapted to carry out an orbital movement over the outer surface of the members and to move close to the welds and be oriented relative to the latter, and further comprising:
    a fixed open U-shaped squirrel-cage structure, fixed jacks adapted to position said fixed squirrel-cage structure transversely astride one of said members and to fix said squirrel-cage structure to said member, said squirrel-cage structure being adapted to be coaxially aligned with the theoretical axis of said member, and guide roller tracks open as a U, included in said fixed structure;
    a movable structure also in open U-shaped squirrel-cage form, guided by said roller tracks and adapted to rotate inside the fixed structure,
    a radially adjustable retractable sleeve, borne by said movable structure parallel to its axis;
    an arm sliding inside said sleeve; and
    one or more orientable measuring heads, borne at the end of said arm by a wrist endowed with several degrees of freedom for orienting said heads; wherein
    the examining probes are fixed to said head and are adapted to be brought into contact with the members to be checked.

2. Scanner according to claim 1, including means to position the end of the arm to follow the theoretical curve defined by the intersection between the cylinder generated by the orbital movement of the arm extending from the sleeve and the bisector between the tangents to the members contained in the plane perpendicular to the weld bead for each point thereof.

3. Scanner device according to claim 2 comprising means for inspecting the bead simultaneously on the two members on each side of the weld comprising the member on which the scanner is fixed and the intercepting member; wherein the wrist is oriented towards the bead along the bisector of the tangents to the two members contained in the plane perpendicular to the bead at the point concerned; wherein a slide table having an upper plate and a lower plate connects the wrist and arm and supports at least two of said measuring heads, said plates being respectively parallel to the tangents to each of the members and having an inclination to the bisector varying progressively with the orbital movement of the arm; wherein the plates regulate the longitudinal movement of the probes to bring them into contact with the weld bead; wherein the perpendicular plane defined by the axes of the wrist and that of the plates is merged with the plane perpendicular to the tangent to the bead at the point concerned; wherein the geometric manufacturing tolerances are taken into consideration by a cross-movement of one of the plates; and wherein this movement is servo-coupled to the indications of a joint follower.

4. Scanner device according to claim 1, further comprising a slide table connecting the wrist and arm for supporting the measuring head with cross movements in the direction of the arm and radially pivoting on itself to remain facing weld, wherein the head is provided with two degrees of freedom to compensate for manufacturing tolerances.

5. Scanner device of claim 1, wherein the table further includes a joint follower for adjusting the position of the probes to a precise and constant distance of the weld bead.

* * * * *